US00PP21468P2

(12) United States Plant Patent
Eskelund

(10) Patent No.: US PP21,468 P2
(45) Date of Patent: Nov. 16, 2010

(54) ROSE PLANT NAMED 'EVERA209'

(50) Latin Name: *Rosa hybrida*
Varietal Denomination: Evera209

(75) Inventor: Rosa Eskelund, Fåborg (DK)

(73) Assignee: Roses Forever ApS, Faborg (DK)

( * ) Notice: Subject to any disclaimer, the term of this patent is extended or adjusted under 35 U.S.C. 154(b) by 0 days.

(21) Appl. No.: 12/462,522

(22) Filed: Aug. 5, 2009

(51) Int. Cl.
*A01H 5/00* (2006.01)

(52) U.S. Cl. ..... Plt./117
(58) Field of Classification Search ..... Plt./117, Plt./124, 103
See application file for complete search history.

*Primary Examiner*—June Hwu
(74) *Attorney, Agent, or Firm*—C. A. Whealy

(57) ABSTRACT

A new and distinct cultivar of Rose plant named 'Evera209', characterized by its upright and mounding plant habit; dark green-colored leaflets; fragrant double white-colored flowers; flowers held upright on strong and erect peduncles; and good postproduction longevity.

3 Drawing Sheets

Botanical designation: *Rosa hybrida.*
Cultivar denomination: 'EVERA209'.

BACKGROUND OF THE INVENTION

The present Invention relates to a new and distinct cultivar of Rose plant, botanically known as *Rosa hybrida*, commercially used as a potted Rose, and hereinafter referred to by the name 'Evera209'.

The new Rose plant is a product of a planned breeding program conducted by the Inventor in Fåborg, Denmark. The objective of the breeding program was to develop new uniform potted Rose varieties with novel and attractive flower colors, disease resistance and excellent postproduction longevity.

The new Rose plant originated from a cross-pollination made by the Inventor in October, 2005 of two unnamed proprietary Rose selections, not patented. The new Rose plant was discovered and selected by the Inventor in November, 2006 as a single flowering plant within the progeny of the stated cross-pollination in a controlled greenhouse environment in Fåborg, Denmark.

Asexual reproduction of the new Rose plant by cuttings in a controlled greenhouse environment at Fåborg, Denmark since September, 2008, has shown that the unique features of this new Rose plant are stable and reproduced true to type in successive generations of asexual reproduction.

SUMMARY OF THE INVENTION

The following traits have been repeatedly observed and are determined to be the unique characteristics of 'Evera209'. These characteristics in combination distinguish 'Evera209' as a new and distinct cultivar of Rose:

1. Upright and mounding plant habit.
2. Dark green-colored leaflets.
3. Fragrant double white-colored flowers.
4. Flowers held upright on strong and erect peduncles.
5. Good postproduction longevity.

Plants of the new Rose differ from plants of the parent selections in growth habit as plants of the new Rose are more uniform than plants of the parent selections.

Plants of the new Rose can be compared to plants of the Rose 'Evera 104', disclosed in U.S. Plant Pat. No. 16,846. In side-by-side comparisons conducted in Fåborg, Denmark, plants of the new Rose differed from plants of 'Evera 104' in the following characteristics:

1. Plants of the new Rose were fragrant whereas plants of 'Evera 104' were not fragrant.
2. Plants of the new Rose had larger flowers than plants of 'Evera 104'.
3. Flowers of plants of the new Rose had more petals than flowers of plants of 'Evera 104'.

BRIEF DESCRIPTION OF THE PHOTOGRAPHS

The accompanying colored photographs illustrate the overall appearance of the new Rose plant, showing the colors as true as it is reasonably possible to obtain in colored reproductions of this type. Colors in the photographs may differ slightly from the color values cited in the detailed botanical description which accurately describe the colors of the new Rose plant.

The photograph on the first sheet comprises a side perspective view of a typical plant of 'Evera209' grown in a container.

The photograph on the second sheet is a close-up view of a typical flower of 'Evera209'.

The photograph on the third sheet is a close-up view of the upper surface of a typical leaf, the lower surface of a typical leaf and a typical flower bud (bottom to top).

DETAILED BOTANICAL DESCRIPTION

Plants of the new Rose have not been observed under all possible environmental conditions. The phenotype may vary somewhat with variations in environment such as temperature and light intensity, without, however, any variance in genotype. The aforementioned photographs, following observations and measurements describe plants grown during the spring in Sabro, Denmark, in a glass-covered greenhouse and under commercial potted Rose production practices. Plants were grown in 10-cm containers, pinched two times and were nine to twelve weeks old when the photographs and description were taken. During the production of the plants, day temperatures averaged 21° C., night temperatures averaged 19° C. and light levels ranged from 8,000 to 10,000 lux. In the following description, color references are made to The Royal Horticultural Society Colour Chart, 2007 Edition, except where general terms of ordinary dictionary significance are used.

Botanical classification: *Rosa hybrida* 'Evera209'.

Parentage:

*Female, or seed, parent.*—Unnamed proprietary selection of *Rosa hybrida*, not patented.

*Male, or pollen, parent.*—Unnamed proprietary selection of *Rosa hybrida*, not patented.

Propagation.—

*Type.*—By cuttings.

*Time to initiate roots, summer.*—About twelve days at 24° C.

*Time to initiate roots, winter.*—About twelve days at 21° C.

*Time to produce a rooted young plant, summer.*—About 28 days at 24° C.

*Time to produce a rooted young plant, winter.*—About 32 days at 24° C.

*Root description.*—Fibrous, fine to thick; white in color.

*Rooting habit.*—Freely branching; moderately dense.

Plant description:

*Plant form.*—Upright and mounding plant habit.

*Growth habit.*—Moderately vigorous.

*Branching habit.*—About two lateral branches develop; pinching enhances lateral branch development.

*Plant height.*—About 16 cm to 20 cm.

*Plant width* (*spread*).—About 15 cm to 18 cm.

*Lateral branches.*—Length: About 14 cm to 18 cm. Diameter: About 3 mm. Internode length: About 1 cm to 1.5 cm. Strength: Strong. Texture: Smooth, glabrous. Color: Close to 137C. Thorns: Density: About two to five per linear centimeter. Shape: Triangular with sharp acuminate apices. Height: About 2 mm to 4 mm. Diameter, at base: About 1 mm to 2 mm. Color, immature: Close to 145B to 145C. Color, mature: Close to 165C.

Foliage description:

*Arrangement.*—Alternate; compound with three or five leaflets per leaf.

*Leaf length.*—About 6 cm to 10 cm.

*Leaf width.*—About 5 cm to 7 cm.

*Terminal leaflet length.*—About 4 cm to 5 cm.

*Terminal leaflet width.*—About 2 cm to 3 cm.

*Lateral leaflet length.*—About 2.5 cm to 4 cm.

*Lateral leaflet width.*—About 1.5 cm to 2.5 cm.

*Leaflet shape.*—Ovate.

*Leaflet apex.*—Acute.

*Leaflet base.*—Obtuse to rounded.

*Leaflet margin.*—Serrulate.

*Leaflet texture, upper and lower surfaces.*—Smooth, glabrous; leathery.

*Leaflet venation pattern.*—Pinnate; reticulate.

*Leaflet color.*—Developing leaflets, upper surface: Close to 137A to 137B. Developing leaflets, lower surface: Close to 147B. Fully developed, upper surface: Darker than N137A; venation, close to 144B. Fully developed, lower surface: Close to 147B; venation, close to 146D.

*Petioles.*—Leaf petiole length: About 1.5 cm to 2.5 cm. Leaf petiole diameter: About 1 mm. Leaflet petiole length: About 2 mm. Leaflet petiole diameter: About 1 mm. Leaf petiole texture, upper and lower surfaces: Smooth, glabrous. Leaflet petiole texture, upper and lower surfaces: Smooth, glabrous. Leaf petiole color, upper surface: Close to 146A. Leaf petiole color, lower surface: Close to 146B. Leaflet petiole color, upper surface: Close to 146B. Leaflet petiole color, lower surface: Close to 146C.

*Stipules.*—Quantity: Two per leaf. Length: About 3 mm to 5 mm. Width: About 0.5 mm to 1 mm. Shape: Lanceolate. Apex: Acuminate. Base: Truncate; sessile. Margin: Mostly entire; ciliate. Texture, upper and lower surfaces: Smooth, glabrous; leathery. Color, upper surface: Close to 146A. Color, lower surface: Close to 146A to 146B.

Flower description:

*Flower type and habit.*—Large double flowers with numerous petals; consistently symmetrical rosette flowers; flowers borne on strong and erect peduncles with one terminal flower per lateral branch.

*Flowering season.*—Year-round under greenhouse conditions, optimal flowering from spring through autumn under garden conditions; flowering intermittent; plants begin flowering about 78 days after planting.

*Flower longevity on plant.*—About three weeks; flowers persistent.

*Fragrance.*—Fragrant; pleasant.

*Flower diameter.*—About 4 cm to 5 cm.

*Flower depth* (*height*).—About 3.5 cm.

*Flower buds.*—Shape: Ovoid. Length: About 1.5 cm. Diameter: About 1.2 cm. Color: Between 144A and 137C.

*Petals.*—Quantity: Numerous; about 125 per flower arranged in numerous whorls. Length: About 2.5 cm to 3.5 cm. Width: About 1.8 cm to 4.5 cm. Shape: Obovate to broadly obovate. Apex: Rounded and cuspidate. Base: Attenuate. Margin: Entire. Texture, upper and lower surfaces: Smooth, glabrous; satiny. Color: When opening, upper surface: Close to NN155B. When opening, lower surface: Close to NN155A. Fully opened, upper and lower surfaces: Close to NN155D.

*Sepals.*—Quantity per flower: Typically five. Length: About 2.5 cm to 3 cm. Width: About 6 mm to 7 mm. Shape: Lanceolate. Apex: Pointed, caudate. Base: Truncate. Margin: Entire. Texture, upper and lower surfaces: Pubescent; leathery. Color: When opening, upper surface: Close to 191A. When opening, lower surface: Close to 146B. Fully expanded, upper surface: Close to 191A. Fully expanded, lower surface: Close to 146A to 146B.

*Peduncles.*—Strength: Moderately strong to strong; flexible. Aspect: Erect. Length: About 3.5 cm to 4 cm. Diameter: About 3.5 mm. Texture: Smooth, glabrous. Color: Close to 144A.

*Reproductive organs.*—Stamens: Quantity per flower: About five. Anther length: About 1 mm to 1.5 mm. Anther shape: Reniform. Anther color: Close to 151B. Filament color: Close to 145D. Pollen amount: None observed. Pistils: Quantity per flower: About 40. Pistil length: About 4 mm to 6 mm. Stigma color: Close to 150C. Style length: About 2 mm to 3 mm. Style color: Close to 145D. Receptacle shape: Cup-shaped. Receptacle height: About 1 cm. Receptacle diameter: About 1 cm. Receptacle texture: Smooth, glabrous.

Receptacle color: Close to 144A. Seed/fruit: Seed and fruit production has not been observed.

Pathogen/pest resistance: Plants of the new Rose have not been observed to be resistant to pathogens and pests common to Roses.

It is claimed:

1. A new and distinct Rose plant named 'Evera209' as illustrated and described.

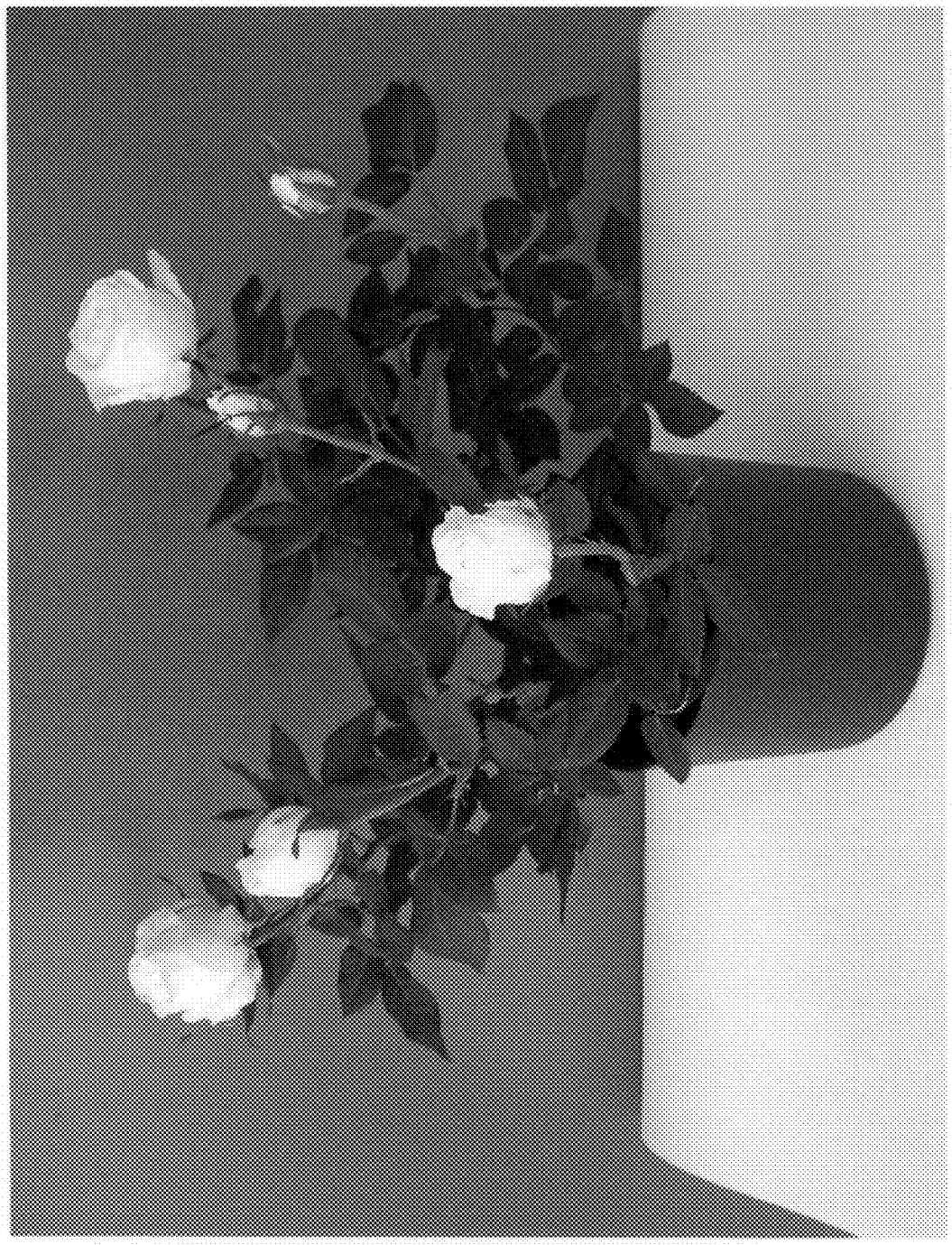

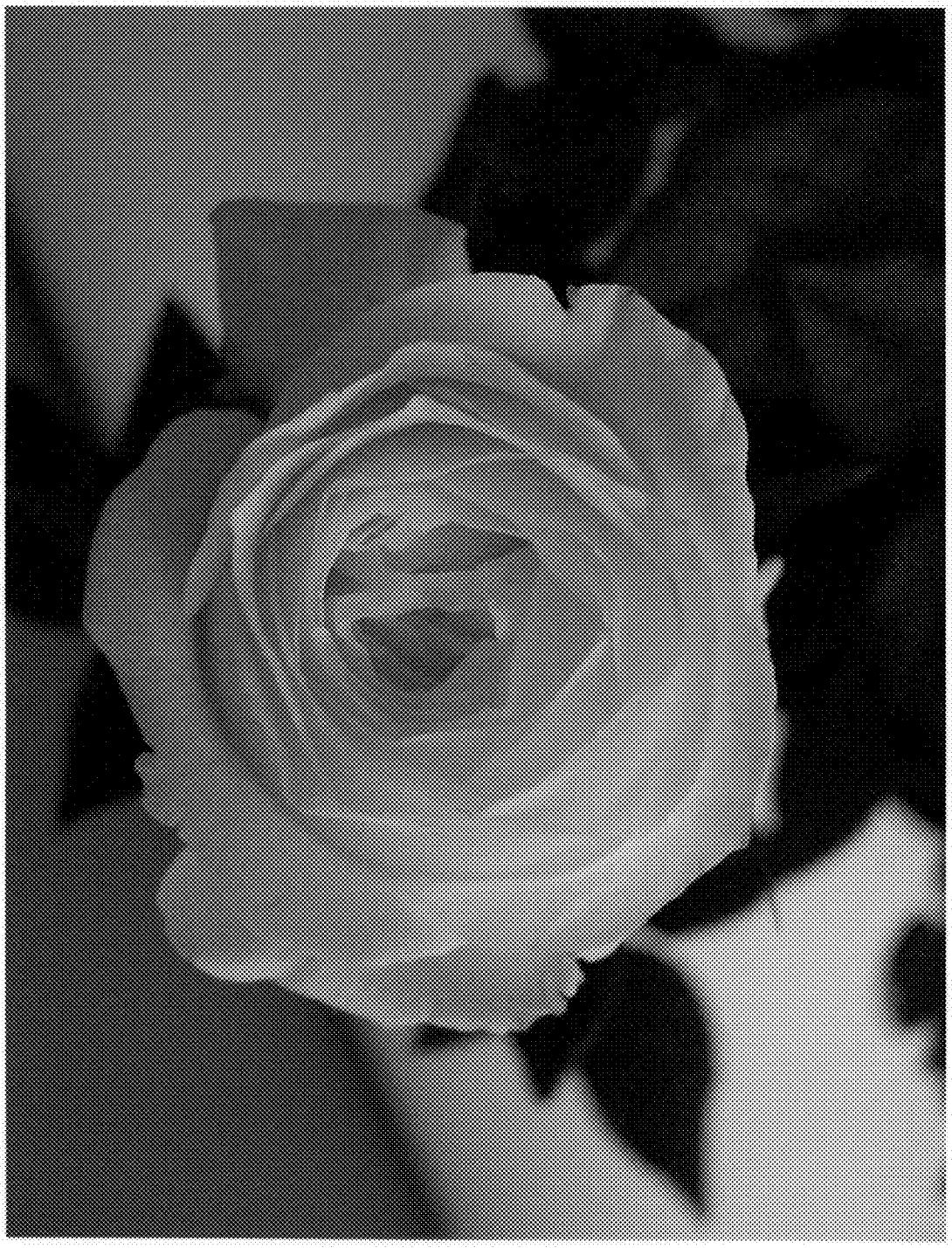

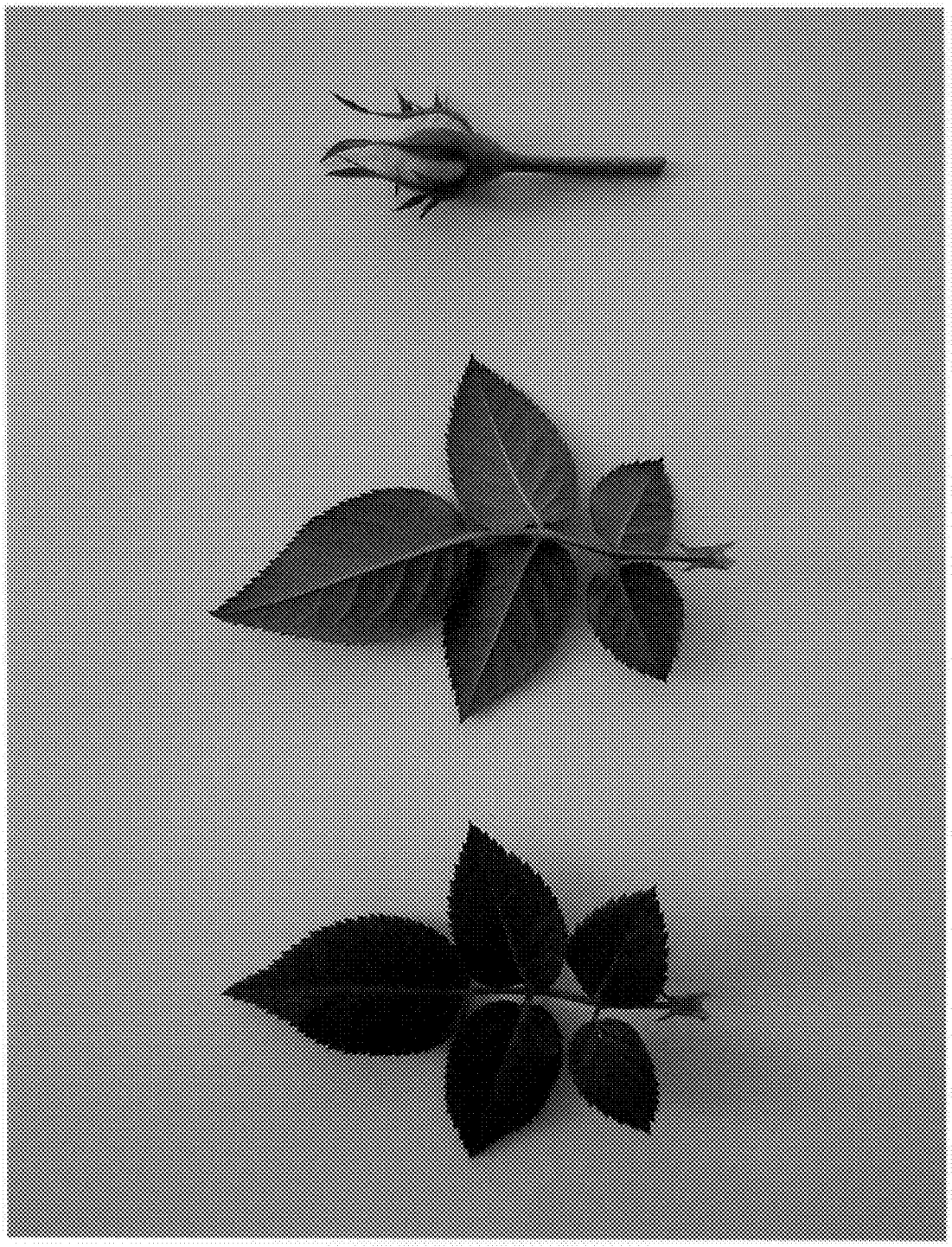

* * * * *